(12) United States Patent
Kehoe

(10) Patent No.: US 6,231,500 B1
(45) Date of Patent: *May 15, 2001

(54) ELECTRONIC ANTI-STUTTERING DEVICE PROVIDING AUDITORY FEEDBACK AND DISFLUENCY-DETECTING BIOFEEDBACK

(76) Inventor: Thomas David Kehoe, 18510 Decatur Dr., Monte Sereno, CA (US) 95030-3088

( * ) Notice: Subject to any disclaimer, the term of this patent is extended or adjusted under 35 U.S.C. 154(b) by 0 days.

This patent is subject to a terminal disclaimer.

(21) Appl. No.: 08/434,024

(22) Filed: May 2, 1995

Related U.S. Application Data

(63) Continuation-in-part of application No. 08/216,630, filed on Mar. 22, 1994, now Pat. No. 5,794,203.
(51) Int. Cl.[7] ....................................................... A61F 5/58
(52) U.S. Cl. ............................................. 600/23; 704/271
(58) Field of Search .............................. 600/23; 128/905; 704/271

(56) References Cited

U.S. PATENT DOCUMENTS

| | | | | |
|---|---|---|---|---|
| 3,566,858 | * | 3/1971 | Larson | 600/23 |
| 4,685,448 | * | 8/1987 | Shames et al. | 600/23 |
| 4,784,115 | * | 11/1988 | Webster | 600/24 |

* cited by examiner

*Primary Examiner*—John P. Lacyk

(57) ABSTRACT

Improvements to a biofeedback device for treating stuttering are disclosed. The device monitors aspects of speech production. When stuttering phenomena are detected, the device provides fluency-enhancing auditory feedback to reduce stuttering. As the user develops speech motor skills (typically taught by a speech pathologist), the device senses reduced stuttering phenomena and reduces auditory feedback. When the user can talk fluently without feedback, he discontinues using the device and continues to talk fluently. The improvements disclosed in this continuation-in-part are a biofeedback feature that monitors the user's vocal pitch; micropower impulse radar to monitor the user's muscle activity; and a fluency-enhancing auditory feedback feature that provides the sound of the user's vocal chords without the sounds added by nasal and oral cavities.

4 Claims, 3 Drawing Sheets

ELECTRONIC ANTI-STUTTERING DEVICE PROVIDING AUDITORY FEEDBACK AND DISFLUENCY-DETECTING BIOFEEDBACK

This application is a Continuation-In-Part of, and claims priority from, U.S. patent application Ser. No. 08/216,630, filed Mar. 22, 1994, now U.S. Pat. No. 5,794,203, entitled BIOFEEDBACK SYSTEM FOR SPEECH DISORDERS, and is commonly assigned with the present invention.

BACKGROUND OF THE INVENTION

There are many theories as to the origin, nature, and best treatment of stuttering. Many speech pathologists believe that the root of stuttering is an inability to control the laryngeal muscles.

Speech sounds can be differentiated between voiceless sounds, such as /p/ and /t/, which are produced by the lips, tongue and jaw (the articulation muscles) altering the exhalation of air, and voiced sounds, such as /b/ and /d/, which are similar but also involve vibration of the larynx. This vibration is called phonation.

The larynx vibrates faster than the brain can control muscles—about 125–250 Hz. Phonation is caused by the vocal folds catching in air flowing past them. To phonate, the vocal folds must be neither too relaxed (allowing air to flow past without catching), nor too tense (blocking exhalation).

Most words contain both voiced and voiceless sounds, so a normal speaker will start and stop phonation many times per second. Persons who stutter have poor laryngeal control, usually tensing their vocal folds too tightly. Unable to move from a voiceless sound to a voiced sound, the person will repeat or prolong the voiceless sound ("c-c-c-c-cat"), or add an unrelated voiced sound to start phonation, ("ah, cat"), or not make any sound—a silent block. The person may try to push through the blocked larnyx by tensing neck or facial muscles.

The larynx is one of the first muscles people tense when experiencing fear or anxiety. Thus stuttering is often associated with fear and anxiety.

The most widely-practiced stuttering therapy is fluency-shaping therapy. A speech pathologist trains a person who stutters to:

Breathe with his diaphragm, which relaxes respiration muscles, and produces the gentle, steady airflow necessary for phonation.

Gently increase vocal volume, and so laryngeal vibration, at the beginning of each phrase (gentle onset).

Continue phonation through the end of the phrase, without stopping (continuousphonation), by keeping the vocal folds relaxed and air flowing.

Speak slower, with prolonged vowel sounds, to enable continuous phonation (all vowels are voiced).

Reduce articulatory pressure, by relaxing the lips, tongue, and jaw, and de-emphasizing voiceless consonants (produced by these articulation muscles) which interrupt phonation.

Fluency-shaping therapy begins by teaching these speech motor skills in the clinical environment. The speech pathologist models the behavior, and provides verbal feedback as the person learns to perform the motor skill.

At first, the target speech behaviors are exagerated, producing abnormally slow, monotonous, but relaxed and fluent speech. As the person develops speech motor control, he increases rate and prosody until his speech sounds normal.

When the person's speech is fluent and sounds normal in the clinical environment, he works with the speech pathologist the transfer these speech motor skills to his everyday life.

Fluency-shaping stuttering therapy is effective for about 70–75% of adults who stutter (and more effective for children who stutter), according to recent research[1].

[1]Boberg, E., Kullyn D., "Long-Term Results of an Intensive Treatment Program for Adults and Adolescents Who Stutter," *Journal of Speech and Hearing Research;* October 1994, 37(5)

There are two broad reasons for the failure of fluency-shaping stuttering therapy:

1) the person never develops the target speech motor skills in the clinical environment;
2) the person never transfers the target speech motor skills to his everyday life.

A variety of electronic devices are available to aid both of these goals. Electronic devices can also reduce the fear and anxiety associated with stuttering.

These electronic devices can be divided into three main classes:

1) Devices which enable immediate fluency, without training or mental effort.
2) Motoric audition devices, which alter speech muscle activities by altering vocal perception.
3) Biofeedback devices, which develop awareness and control of speech motor skills.

Immediate Fluency Devices

Several types of auditory feedback reduce stuttering immediately, without training or mental effort.

Researchers have hypothesized that these devices correct an undiscovered defect in the auditory systems of persons who stutter.[2]

[2]Wolf, A. A., Wolf, E. G. (1959). "Feedback processes in the theory of certain speech disorders." *Speech Pathology and Therapy,* 2, 48–55; Mysak, E. D. (1960). "Servo-theory and stuttering." *Journal of Speech and Hearing Disorders,* 25, 188–195; Yates, A. J. (1963). "Recent empirical and theoretical approaches to the experimental manipulation of speech in normal subjects and in stammerers." *Behaviour Research and Therapy,* 1, 95–119; Butler, B. R., Stanley, P. E., (1966). "The stuttering problem considered from an automatic control point of view." *Folia Phoniatricia,* 18, 33–44; Webster, R. L. & Lubker, B. B. (1968). "Interrelationships among fluency producing variables in stuttered speech." *Journal of Speech and Hearing Research,* 11, 754–766.

Alternatively, a normal auditory function, while not causing stuttering, may impede overcoming stuttering. This is the stapedius muscle reflex of the middle ear. This muscle attenuates vocal perception 5–15 dB.[3] This impairment in hearing your voice impairs changing how you talk.

[3]Shlomo Sillman, *The Acoustic Reflex* (1984). San Diego: Academic Press.

Improved vocal awareness improves vocal control. All of the following devices improve aspects of vocal awareness and control:

1) Delayed auditory feedback (DAF) in the 25–75 ms range delays your voice (in your headphones) just long enough to overcome the stapedius muscle reflex, but is not so long that your voice is perceived as an echo. The device reduces stuttering 75–85%.[4]

2) Frequency-altered auditory feedback (FAF) alters the pitch of your voice (in your headphones), typically ½ octave. The device reduces stuttering 75–85%.[5]

3) Laryngeal auditory feedback (LAF) provides the sound of your larynx to your ears without the sounds added by your nasal and oral (tongue and lips) cavities. This can be accomplished in several ways. The Fluency Master (U.S. Pat. No. 4,784,115) tapes a microphone to your neck, and then amplifies your voice in a hearing-aid type amplifier. The device reduces stuttering in 30–80% of users.[6] The Edinburgh Masker (U.S. Pat. No. 3,566,858 and U.S. Pat. No. 3,773,032) electronically remove the sounds added by your nasal and oral cavities, providing only a sound similar to your laryngeal vibration. This device reduces or eliminates stuttering in about 90% of users.[7]

[4]Kalinowski, J., Armson, J., Stuart, A., Gracco, V., Roland-Mieszkowski, M. "Effects of alterations in auditory feedback and speech rate on stuttering frequency." Language and Speech, 1993, 36, 1–16.
[5]Ibid.
[6]The device reduces stuttering immediately in 30% of users. An additional 50% benefit after 4 hours of therapy. Webster, R., Stigora, W. "Technology and Fluency-Building With Various Patient Populations." Presented at American Speech-Language Hearing Association annual convention, November, 1991. The Fluency Master is made by GN Danavox, 5600 Rowland Road, Suite 250, Minnetonka, Minn. 55343.
[7]Dewar, Dewar, Austin, Brash. "Long Term Use of An Automatically Triggered Auditory Feedback Masking Device in the Treatment of Stammering." British Journal of Disorders of Communication, Vol. 14, No. 3: The device "was found to be effective in abolishing or greatly reducing stammering in 89% of 195 cases. The effectiveness of the portable device has continued in the majority of users during periods of observation of up to three year. In a follow-up study of 67 subjects with six months or more experience of the Masker . . . 67% stated that, as a result of using the device, their unaided speech fluency had improved." Herbert Goldberg of the Foundation for Fluency (Skokie, Ill.) writes privately: "I am in contact with over 500 people who use or have used the [Edinburgh] Masker. In most cases the end result is the person uses the device less and less as time passes due to less need for it." The Edinburgh Masker is no longer manufactured.

Therapy Protocol

The above devices may be used in therapy to train you to talk fluently, and no longer need to use a device.

First, the device is used to establish control of your speech.

Next, you learn fluency-shaping speech motor skills from a speech pathologist.

The device then helps you use these speech motor skills in everyday life. The device also reduces speech-related fear and anxiety, such as fear of telephones.

Then you switch off the device for short periods of time in relaxed situations, and continue to use your fluency-shaping speech motor skills.

Next, you switch off the device for longer periods of time, and in more stressful situations. Alternatively, the biofeedback technologies described below can automatically reduce auditory feedback as they detect improved fluency.

When you can talk fluently anywhere with the device switched off, you no longer need it.

Motoric Audition Devices

Some types of auditory feedback alter your speech motor activities. These devices include:

Delayed auditory feedback (DAF) in the 125–250 ms range. You hear an echo of your voice in headphones. This forces you to prolong vowel sounds, and continuously vibrate your vocal folds (continuous phonation). This can completely eliminate stuttering. A 125–150 ms delay slows speech slightly, and sounds thoughtful and confident. A 150–250 ms delay slows speech considerably, and sounds robotic and monotonous. Long-delay DAF is useful in training the slow speech target in the clinic.[8] However, users refuse to talk abnormally slowly outside the clinic, so long-delay DAF has little value in transferring fluency.

Metronomes can also help you prolong vowel sounds, similar to long-delay DAF.[9]

A downward frequency-altered auditory feedback (FAF) shift slows down your speech slightly, and an upward pitch shift increases speaking rate slightly. These effects are too mild to produce carryover fluency.

White noise masking auditory feedback (MAF) provides a random frequency noise to your ear, eliminating auditory perception. You then must talk by feel, and so improves proprioceptive awareness (the awareness of physical sensations of speech muscle activity). The device reduces stuttering moderately (about 35%), but requires volumes high enough to cause hearing damage.[10]

[8]Ryan and Van Kirk. "Establishment of fluent speech in 50 stutterers using DAF and operant procedures." Journal of Speech and Hearing Disorders, February 1974; 39(1): DAF therapy reduced stuttering from an average 9.2 stutters per minute to 0.2 stutters per minute in about 20 hours of therapy over four months. Of 50 subjects, 30 reached the carryover stage and no longer needed DAF, 3 were still in the transfer stage, and 17 dropped out due to work conflicts, etc.
[9]Brady, J. P. "A behavioral approach to the treatment of stuttering." American Journal of Psychiatry, 125, 843–848, 1968: 67% average reduction in stuttering, 91% of subjects had substantial improvement. Wohl, M. "The electronic metronome: an evaluative study." British Journal of Communicative Disorders, 3, 89–98, 1968.
[10]Kalinowski, J., Armson, J., Stuart, A., Gracco, V., Roland-Mieszkowski, M. "Effects of alterations in auditory feedback and speech rate on stuttering frequency." Language and Speech, 1993, 36, 1–16.

Biofeedback Devices

There are biofeedback devices to monitor every physical aspect of speech. These devices provide information faster and more accurately than a therapist. Some devices are portable and can be used away from the clinic.

Some devices provide information that a therapist can never provide, e.g., electromyography (EMG) displays the activity of individual muscles.

Biofeedback devices include:

Respiration can be monitored via a chest strap.

Gentle onset devices, such as the Voice Monitor used in the Precision Fluency Shaping Program, train you to gradually increase vocal volume at the beginning of phrases, and maintain a constant volume through the end of the phrase. This is accomplished with continuous phonation.

Vocal pitch biofeedack trains you to speak with a lower vocal pitch. You accomplish this with diaphragmatic breathing, slow speech, continuous phonation, and relaxed articulation muscles.

Electromyographs (EMG) monitor muscle activity via electrodes taped to your neck and jaw. The device trains you to breathe with your diaphragm, speak slowly, continuously phonate, and talk with relaxed articulation muscles. Two studies of EMG stuttering therapy found a 40–70% long-term reduction in stuttering, after just 5–20 hours of therapy.[11]

Electroglottographs measure vocal fold activity through electrodes taped to the neck.[12]

Galvanic skin response (GSR) devices crudely measure general relaxation. Radio Shack sells a GSR biofeedback device for $15.

Other devices monitor air velocity, tongue placement, nasality, etc.[13]

Biofeedback devices usually provide visual feedback, either a computer monitor or a row of green, yellow, and red lights. You try to keep the green lights on, or to produce a certain pattern on the computer monitor. Some computer-based devices even have video games.

The speech pathologist first teaches the person to perform the target motor skill (diaphragmatic breathing, gentle onset, etc.), while watching the visual display. When you have accomplished this, the therapist reduces visual feedback until the person can perform the motor skill without using the biofeedback device. The person can then discontinue using the device and continue to talk fluently.

[11]Craig, Cleary, "Reduction of stuttering by young male stutterers using EMG feedback," Biofeedback and Self Regulation, September 1982; 7(3): 241–55; Manschreck, Kalotkin, Jacobson, "Utility of electromyographic biological feedback in chronic stuttering: a clinical study with follow-up," Perception and Motor Skills October 1980; 51(2): 535–40.

[12]Gow, M. L., Ingham, R. J. "Modifying electroglottograph-identified intervals of phonation: the effect on stuttering." *Journal of Speech and Hearing Research* June 1992; 35(3):495–511.
[13]Contact Kay Elemetrics (Pine Brook, N.J.) or see to the *ASHA Buyer's Guide*.

Integrated Stuttering Therapy Systems

Three systems combine several technologies:

The Visi-Pitch (Kay Elemetrics) is a computer-based system providing visual display of vocal pitch and amplitude. The system also provides delayed auditory feedback (DAF). The device includes measurement tools, statistical analysis, and video game visual feedback.[14]

The Computer-Aided Fluency Establishment and Trainer (CAFET) combines a respiration monitor (chest strap) with vocal volume rate-of-change (gentle onset), to train seven fluency shaping skills. The system is computer-based. Visual feedback includes video games. Initially, both a graphical display of the your speech and text error messages are displayed. Then the graphical display is switched off, and only error messages appear. Lastly, no visual feedback is provided until the speech task is completed, and then error messages are displayed. This trains you to talk fluently after discontinuing use of the device. One study found that 92% of users were fluent two years after completing the therapy program.[15]

The Biofeedback System For Speech Disorders (made by Casa Futura Technologies, of Monte Sereno, Calif., patent application Ser. No. 08/216,630, filed Mar. 22, 1994) bridges the gap between the effective but large and expensive clinical devices (such as the Visi-Pitch and CAFET) and the small, affordable, but too often ineffective consumer devices (such as the Fluency Master and Edinburgh Masker). The device is portable, providing DAF, FAF, and EMG biofeedback. When the device detects stuttering, it switches on DAF. If it detects severe stuttering, it alters the DAF pitch, providing FAF. When the device detects on-target fluent speech, it switches off auditory feedback. As you develop your fluency shaping motor skills, the device automatically switches itself off, until you no longer need to use the device. The device also plugs into telephones.

[14]Cronk, Cynthia. "Clinical application of microcomputer technology in the treatment of stuttering." (1986) Kay Elemetrics, P.O. Box 2025, Pine brook, N.J. 07058.
[15]The "criteria for success" was less than 1.4% stuttered syllables, at a speaking rate of 3.5 syllables per second. At six months post-therapy 82% of subjects met the criteria; at twelve months, 89%; at 2 years, 92%. Reported by CAFET, Inc., 4208 Evergreen Lane, Suite 213, Annandale, Va. 22003.

SUMMARY OF THE INVENTION

The objectives of this invention are improvements on the Biofeedback System for Speech Disorders (patent application Ser. No. 08/216,630, filed Mar. 22, 1994). This latter invention is described above (the last paragraph of the section "Background of the Invention").

The first improvement is an alternative to the electromyographic (EMG) disfluency detector described in earlier application. The alternative is to measure a user's vocal pitch. This is accomplished with a frequency-to-voltage converter. Speaking with a lower vocal pitch requires diaphragmatic breathing, slower speech, and relaxed laryngeal and articulation muscles. These are the motor skills taught in stuttering therapy. The vocal pitch detector effectively monitors whether a person is accomplishing the goals of stuttering therapy.

A second alternative to EMG biofeedback, for monitoring a user's muscle activity to detect disfluency, is micropower impluse radar (MIR). MIR is short-range radar, using commonly-available microchips, invented by Tom McEwan of Lawrence Livermore National Laboratory, of Livermore, Calif. Unlike other radar, MIR is small and inexpensive. A user could tape a small sensor to his throat, which would monitor laryngeal activity.

The next improvement is an alternative to delayed auditory feedback (DAF), frequency-altered auditory feedback (FAF), and masking auditory feedback (MAF) described in the earlier application. The alternative is to provide laryngeal auditory feedback (LAF). Laryngeal auditory feedback provides the sound of the user's vibrating vocal chords (phonation) to the user's ears, without the sounds added by the nasal and oral (tongue and lips) cavities.

There are several methods to accomplish this. One method is to tape a microphone to the user's throat, directly in front of the larynx.

Another method is to attach electroglottograph electrodes to the user's throat, and electrically detect vocal chord activity. This electrical signal can then be converted into an audio signal and provided to the user's ears.

A third method is to receive the user's air-transmitted voice with a standard microphone, but electronically remove the sounds added by the nasal and oral cavities, leaving only the laryngeal sound. This can be accomplished by amplifying the user's voice with so much gain that the amplifier clips the signal. The result is a square wave at the vibrating frequency of the vocal chords.

This square wave may be provided to the user's ear, as it sounds similar to vocal chord vibration. A further refinement uses a phase-locked loop to provide a minimum and maximum frequency. A further refinement converts the square wave to a sine wave (vocal chords produce sine waves).

The latter method was used in the Edinburgh Masker, the popular anti-stuttering device distributed by the Foundation for Fluency (of Skokie, Ill.). (Many people mistakenly believe that the Edinburgh Masker provides white noise masking auditory feedback (MAF), for the purpose of eliminating all auditory perception.)

BRIEF DESCRIPTION OF THE DRAWINGS

For a fuller understanding of the invention, reference is had to the following descriptions taken in connection with the accompanying drawings, in which.

DETAILED DESCRIPTION OF THE PREFERRED EMBODIMENTS

Figure 1:
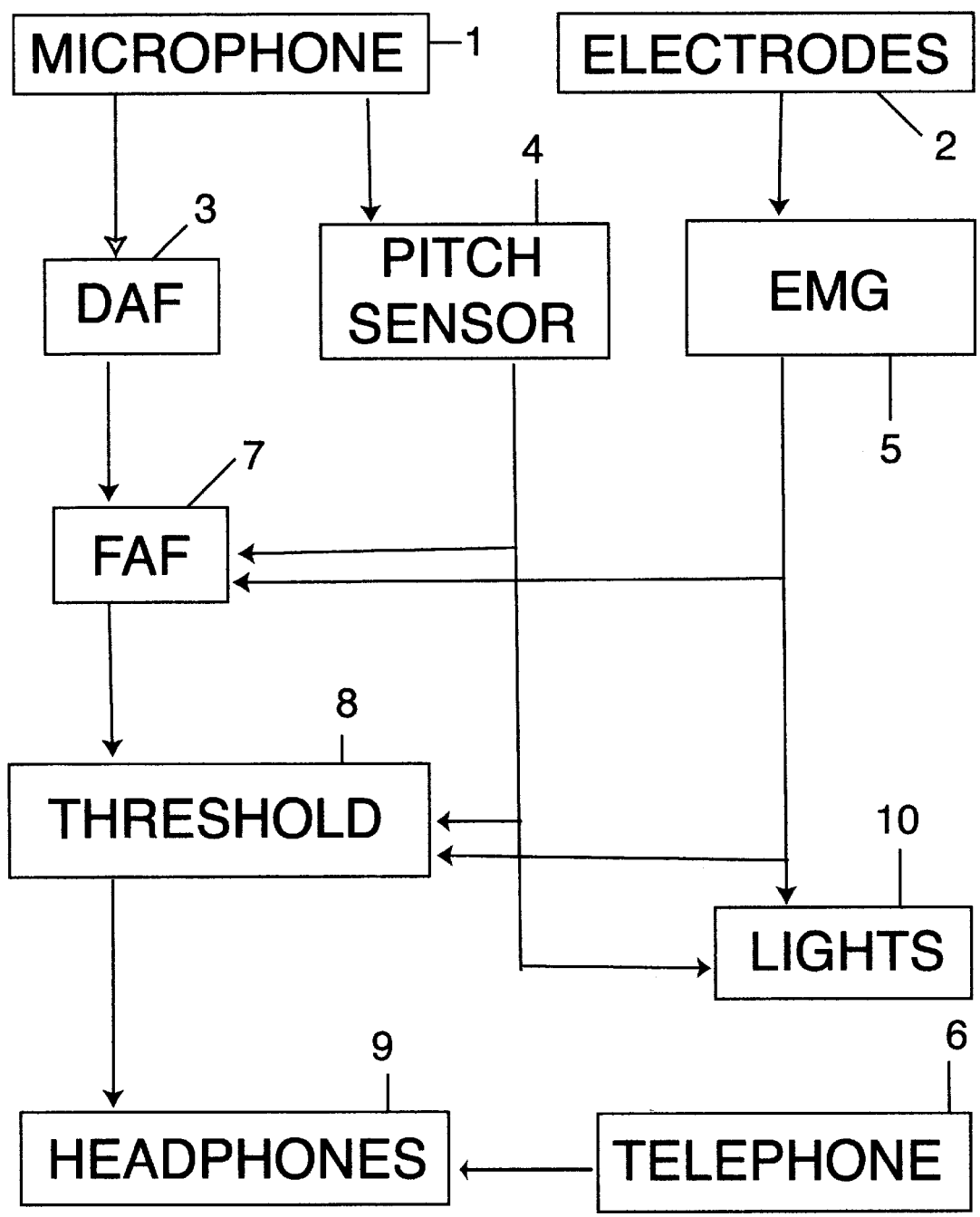
FIG. 1 is a overview of a larger vocal pitch and electromyographic biofeedback device with DAF, FAF, both auditory and visual feedback, and a telephone interface, constructed in accordance with the teachings of the invention.

FIG. 1 shows that a broad overview of a biofeedback system. A user speaks into a microphone (1). The microphone produces an audio signal which goes to three circuits:

a) A delayed auditory feedback (DAF) circuit (3) delays the user's voice.

b) A vocal pitch sensor (4) measures the user's vocal pitch.

c) A voice-operated switch (VOX) circuit (not shown in FIG. 1) switches off a threshold control (8) circuit to cut off sound to the user's ears when the user is not talking. The voice-operated switch circuit also powers down several integrated circuits, to save battery power.

The delayed audio signal, from the DAF circuit (3), then goes to a frequency-altered auditory feedback (FAF) circuit (7), which controls the pitch of the audio signal. The pitch is controlled in accordance with data received from the vocal pitch sensor (4).

The delayed audio signal, from the DAF circuit (3) also goes to a telephone (6).

The delayed, pitch-controlled audio signal from the FAF circuit (7), then goes to a threshold control (8). The threshold control switches the audio signal on or off. The threshold control switches in accordance with data received from the vocal pitch sensor. When the user's vocal pitch is below a target vocal pitch (set by the user), the threshold control switches the audio signal off. When the user's vocal pitch rises above the target vocal pitch (indicating stuttering phenomena), the threshold control switches on the audio signal (to alter the user's speech).

The audio signal from the threshold control (8) then goes to headphones (9) worn by the user.

An audio signal from the telephone (6) also goes to the user's headphones (9).

Sixteen green, yellow, and red lights visually display (10) the user's vocal pitch, using data from the vocal pitch sensor (4).

As an alternative to using the vocal pitch sensor (4), the user may choose to monitor muscle activity with electromyographic (EMG) biofeedback. The user wears EMG electrodes (2) taped to his neck and jaw. The EMG electrodes plug into an EMG (5). The EMG then provides data to the FAF circuit (7), the threshold control (8), and the visual feedback circuit (10).

Figure 2:
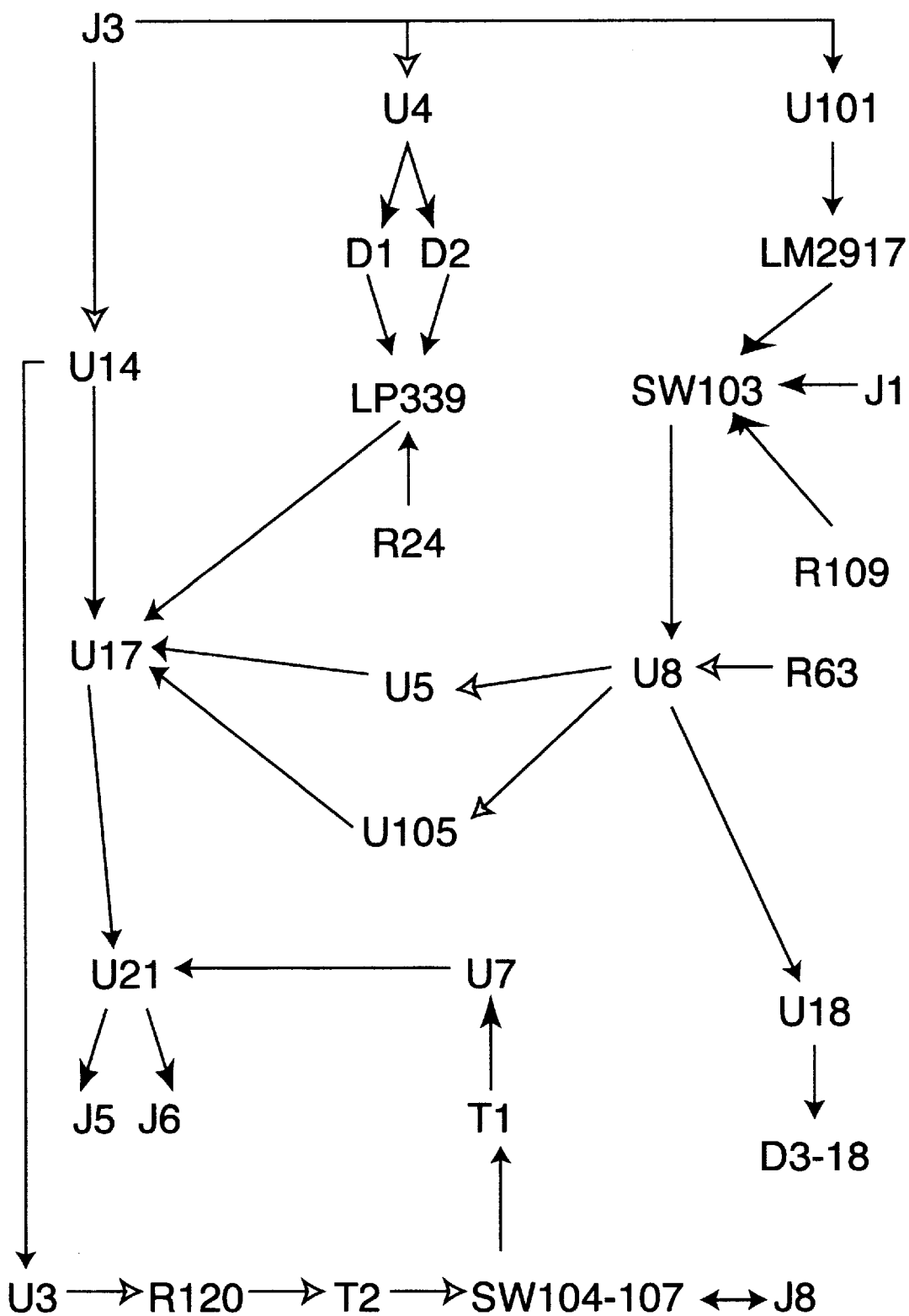
FIG. 2 is an electronic schematic diagram of the device in FIG. 1.

FIG. 2 is an electronic schematic diagram of the biofeedback system in FIG. 1. The components supporting the integrated circuits, such as resistors and capacitors, are used in accordance with designs found in the manufacturers' databooks, and so will not be described in detail.

The user typically wears a headset, with headphones and a microphone. The microphone plugs into 3.5 mm jack J3 (lower middle left of FIG. 2).

Digital delay large-scale integrated circuit (LSI) U14 (a M65831P, made by Mitsubishi, of Japan), delays the audio signal. In this configuration, twelve delays are available, from 20 to 220 milliseconds. The user selects the delay length with 12-position rotary switch SW5. Encoders U19 and U103 (4532, made by Texas Instruments and other manufacturers) encode the signals from the rotary switch into a 4-bit binary number. The 4-bit binary number on U14 pins 4–7 determines the delay length.

Pitch control LSI U17 (a MSM6322, made by OKI, of Japan) controls the pitch of the audio signal. In this configuration, sixteen pitches are available (one octave up or down, in eighth-octave stages). The pitch is selected by a 4-bit binary number on U17 pins 1–3 and 5. The origin of this 4-bit number is explained below.

A 4 MHz clock (U16) runs pitch control device U17, and also runs through divide-by-3 integrated circuit U15 (a 74C107, made by Texas Instruments are other manufacturers). The resulting 1.33 MHz signal drives digital delay U14.

The pitch-controlled, delayed audio signal from pitch-control device U17 is amplified by power amplifier U21 (a MC34119, made by Motorola, of Schaumberg, Ill.). The amplified audio signal then is provided via 3.5 mm jack J5 to the user's headphones. A second 3.5 mm jack J6 is provided for a speech therapist to plug in her headphones.

The audio signal from the microphone also goes to a voice-operated switch. Dual amplifier U4 (an LM358, made by National Semiconductor, of Santa Clara, Calif.) amplifies the signal. The signal is rectified by diodes D1–2. The user may adjust the voice-operated switch threshold (for whispering in a quiet office or yelling at a noisy party) with potentiometer R24. The voice-operated switch signal (signifying that the user is talking or not talking) goes from comparator (¼ of a LP339, made by National Semiconductor, of Santa Clara, Calif.) to the power-down pins of U17 and U21. When the user stops talking, these integrated circuits power down and the user hears no auditory feedback.

The audio signal from the microphone also goes to the pitch sensor circuit. The audio signal is first amplified by dual amplifier U101 (a LM358, made by National Semiconductor, of Santa Clara, Calif.). The gain is about 10 million, so high that the signal clips into a square wave. The square wave is at the vibrating frequency of the user's vocal chords, without the harmonics and sounds added by the user's nasal cavity, lips, tongue, etc.

The square wave drives a tachometer-type input of a frequency-to-voltage converter (an LM2917N-8, made by National Semiconductor, of Santa Clara, Calif.). The voltage output from this integrated circuit is then converted into a 4-bit binary number by analog-to-digital converter U8 (an ADC0804, made by National Semiconductor, of Santa Clara, Calif.). The user sets a target vocal pitch threshold with potentiometer R63.

A below-target vocal pitch switches off the auditory feedback by producing a low (0V) signal on the most-significant digit of the 4-digit number representing the vocal pitch. The most-significant digit is on pin 14 of ADC U8. This data signal is inverted by inverter U5 (¼ of a LP339, made by National Semiconductor, of Santa Clara, Calif.), and then goes to the power-down pins of pitch-control device U17 and power amplifier U21. OR gate U105 (a 4071, made by Texas Instruments and other manufacturers) eliminates interference between the voice-operated switch signal and the vocal pitch threshold signal.

As an alternative to the vocal pitch biofeedback, the user may switch SW103 from frequency-to-voltage converter U102 to 2.5 mm jack J1, into which an electromyograph (EMG) may be plugged. A MyoTrac EMG (made by Thought Technologies, of Montreal, Canada) is suggested. The user's speech-production muscle activity then is monitored instead of the user's vocal pitch.

As a third alternative, the user may switch SW103 to resistor R109. This enables manual control of the FAF function.

The 4-bit number representing the user's vocal pitch is decoded into sixteen signals by decoder U18 (a 74HC154, made by Texas Instruments, and other manufacturers). The sixteen signals light an array of sixteen green, yellow, and red lights (diodes D3–18).

The delayed audio signal from the digital delay LSI U14 also goes to a telephone interface. This audio signal (the user's voice) goes through automatic gain control (AGC) amplifier U3 (a GC4130A, made by Gennum, of Ontario, Canada). This AGC amplifier transmits a constant volume to the telephone, no matter how loudly or quietly the user speaks.

Potentiometer R120 adjusts the transmit volume for different telephones. The audio signal then goes through transformer T2, switches SW104–105, and RJ-22 jack J8 (a standard telephone handset jack) to a telephone.

Four four-posibon switches SW104–107 enable reordering the order of wires in the telephone handset cord. Handset cords have four wires: two for the microphone, and two for the earpiece. Most telephones use the outer wires for the microphone, and the inner wires for the earpiece. The polarity of the microphone wires is not standardized. The polarity of the earpiece wires usually does not matter.

Some telephones, however, use a different order for the microphone and earpiece wires in the handset. Switches SW104–107 can correct any order of wires in the handset.

The user may easily determine the correct positions for switches SW104–107 for any telephone. He plugs his telephone's handset into RJ-22 jack J8. He switches on SW201, connecting a 60 Hz oscillator. He then tries each combination of positions for switches SW106–107, until he hears the oscillator buzzing in the handset's earpiece. Now switches SW106–107 are set correctly to receive an audio signal from the telephone This leaves two possible positions for switches SW104–105. The user plugs his telephone into RJ-22 jack J8, and places the handset off-hook for a dialtone. The user tries each position for SW104–105. One position may have some background buzzing (in the headset), indicating that the polarity is reversed. The switch position in which the dialtone is heard cleanly is correct. The audio signal from the telephone (the caller's voice) goes through RJ-22 jack J8, switches SW106–7, and transformer Ti. The audio signal then goes through AGC amplifier U7 (a GC4130A, made by Gennum, of Ontario, Canada). This AGC amplifier limits the volume in the headphones to 85 dB, complying with federal law. The limited audio signal then is mixed with the auditory feedback signal, amplified by power amplifier U21, and provided to the user's A 5-volt power supply is provided by voltage regulator U22 (an LM2940-5.0, made by National Semiconductor, of Santa Clara, Calif.). A 9-volt battery or a plug-in AC adapter may be used.

Figure 3:
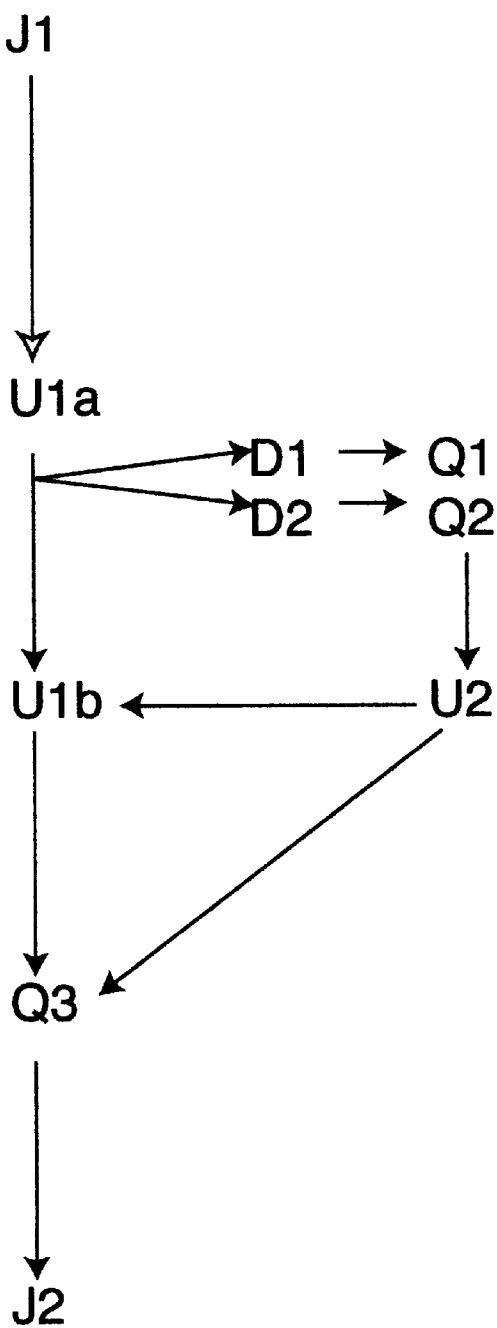
FIG. 3 is an electronic schematic diagram of a smaller, pocket-sized vocal pitch biofeedback system which provides laryngeal auditory feedback (LAF), constructed in accordance with the teachings of the invention.

FIG. 3 is an electronic schematic drawing of a pocket-sized pitch-controlled biofeedback system with laryngeal auditory feedback (LAF).

The user speaks into a microphone. The microphone may be part of a headset (most conveniently put on and off), or taped to a user's throat (more effectively picks up sound produced by the user's vocal chords), or a lapel microphone (least conspicuous). The microphone plugs into 3.5 mm jack J1.

The audio signal from the microphone is amplified by amplifier U1a (½ of a dual LMC6042, made by National Semiconductor, of Santa Clara, Calif.). The gain is adjustable (by the user) from 100 to 1.1 million. This allows for the use of different microphone placements (a throat microphone is much louder than a lapel microphone) or for use in a quiet office vs. a loud party.

The LMC6042 is an extremely low-power dual amplifier. It draws only 20 microamps, and could continuously run from a 9-volt battery for about ten years.

The amplified audio signal then is amplified further by amplifier U1b (½ of a dual LMC6042). The gain is so high that the audio signal is clipped into a square wave. The square wave is at the vibrating frequency of the user's vocal chords (the fundamental vocal tone). The harmonics and sounds added by the nasal cavity and tongue and lips are eliminated.

The square wave then goes to headphones via 3.5 mm jack J2. The user hears auditory feedback similar to the sound of larynx (laryngeal auditory feedback, or LAF). The user may adjust the volume with potentiometer R102.

The amplified audio signal (before conversion into a square wave) is also rectified by diodes D1–2. In combination with transistors Q1–2, this functions as a voice-operated switch (VOX). When the user talks, the transistors switch power on to frequency-to-voltage converter U2 (a LM2917N-8, made by National Semiconductor, of Santa Clara, Calif.). When the user stops speaking, the VOX switches off the auditory feedback, and reduces power consumption.

The square wave produced by amplifier U1b also goes the tachometer-type input of frequency-to-voltage converter U2. An internal comparator switches output on or off depending on the input (measured vocal) frequency, in comparison to a threshold voltage on pin 7. The user sets the threshold voltage, representing his target vocal pitch, with potentiometer R20.

When the measured vocal pitch exceeds the target vocal pitch, the comparator switches on a high (+5 volt) signal to transistor Q3. This switches on the auditory feedback to the headphones, reducing the user's stuttering, and alerting the user that he should relax, take a breath, and talk slower.

Thus, by utilizing the above construction, a biofeedback system can be provided which enables users to talk fluently immediately, and trains them to overcome stuttering and no longer need to use a speech aid.

It will thus be seen that the objects set forth above, among those made apparent from the preceding description, are efficiently attained and, since certain changes may be made in the above constructions without departing from the spirit and scope of the invention, it is intended that all matter contained in the above description or shown in the accompanying drawings shall be interpreted as illustrative, and not in a limiting sense.

It will also be understood that the following claims are intended to cover all of the generic and specific features of the invention, herein described, and all statements of the scope of the invention which, as a matter of language, might be said to fall therebetween.

What is claimed is:

1. A biofeedback system, comprising:

a detector for detecting disfluent speech;

an auditory feedback mechanism for enabling fluent speech; and a controller coupled to said detector and said auditory feedback mechanism, said controller receiving said detection of disfluent speech from said detector and, in response, controlling said auditory feedback mechanism to provide the selective production of auditory feedback in synchronization with said detection of said disfluent speech thereby enabling the production of fluent speech;

wherein said detector for detecting disfluent speech measures vocal pitch.

2. The detector, as claimed in claim 1, wherein said vocal pitch detector comprises a frequency-to-voltage converter.

3. A biofeedback system, comprising:

a detector for detecting disfluent speech;

an auditory feedback mechanism for enabling fluent speech; and a controller coupled to said detector and said auditory feedback mechanism, said controller receiving said detection of disfluent speech from said detector and, in response, controlling said auditory feedback mechanism to provide the selective production of auditory feedback in synchronization with said detection of said disfluent speech thereby enabling the production of fluent speech;

wherein said detector for detecting disfluent speech uses micropower impulse radar (MIR) to monitor muscle activity.

4. A biofeedback system, comprising:

a detector for detecting disfluent speech;

an auditory feedback mechanism for enabling fluent speech; and a controller coupled to said detector and said auditory feedback mechanism, said controller receiving said detection of disfluent speech from said detector and, in response, controlling said auditory feedback mechanism to provide the selective production of auditory feedback in synchronization with said detection of said disfluent speech thereby enabling the production of fluent speech;

wherein said auditory feedback mechanism for enabling fluent speech comprises laryngeal auditory feedback (LAF), providing a sound similar to a user's vocal chord vibrations to said user's ear.

* * * * *